United States Patent [19]
Missbach

[11] Patent Number: 5,641,776
[45] Date of Patent: Jun. 24, 1997

[54] SUBSTITUTED THIOSEMICARBAZONE DERIVATIVES

[75] Inventor: Martin Missbach, Rheinfelden, Switzerland

[73] Assignee: Ciba-Geigy Corporation, Tarrytown, N.Y.

[21] Appl. No.: 500,987

[22] PCT Filed: Nov. 9, 1994

[86] PCT No.: PCT/EP94/03679

§ 371 Date: Jul. 25, 1995

§ 102(e) Date: Jul. 25, 1995

[87] PCT Pub. No.: WO95/14685

PCT Pub. Date: Jun. 1, 1995

[30] Foreign Application Priority Data

Nov. 25, 1993 [CH] Switzerland ............................ 3522/93

[51] Int. Cl.⁶ .................................................. A61K 31/54
[52] U.S. Cl. ........................... 514/227.2; 544/54; 544/55
[58] Field of Search ...................... 544/54, 55; 514/227.2

[56] References Cited

U.S. PATENT DOCUMENTS

| | | | |
|---|---|---|---|
| 4,697,020 | 9/1987 | Stomi et al. ............................ | 548/184 |
| 5,229,405 | 7/1993 | Feige et al. ............................ | 514/369 |

FOREIGN PATENT DOCUMENTS

| | | | |
|---|---|---|---|
| 0508955 | 4/1992 | European Pat. Off. ............... | 514/369 |
| 0508955 | 10/1992 | European Pat. Off. ............... | 514/369 |
| 0573392 | 5/1993 | European Pat. Off. ............... | 514/369 |
| 0573392 | 12/1993 | European Pat. Off. ............... | 514/369 |
| 2035419 | 1/1971 | Germany ................................ | 514/369 |
| 2632747 | 2/1977 | Germany ................................ | 524/369 |

*Primary Examiner*—James H. Reamer
*Attorney, Agent, or Firm*—Ronald J. Campbell; Karen G. Kaiser

[57] ABSTRACT

The present invention relates to novel substituted thiosemicarbazone derivatives of formula (I) wherein $R_1$ is lower alkyl, lower alk-2-en-1-yl, lower alk-2-yn-1-yl, or aryl-lower alkyl, $R_2$ is hydrogen, lower alkyl, aryl, aryl-lower alkyl, lower alk-2-en-1-yl, lower alk-2-yn-1-yl, unsaturated or saturated heterocyclyl-lower alkyl, lower alkoxycarbonyl-lower alkyl or the group —C(=O)—$R_3$, wherein $R_3$ is lower alkyl, aryl, aryl-lower alkyl, aryl-lower alkenyl, heteroaryl (betaryl), aryloxy, aryl-lower alkoxy or lower alk-2-en-1-yloxy, and the salts thereof, to a process for the preparation of said compounds, to pharmaceutical compositions containing them, and to the use thereof as medicaments.

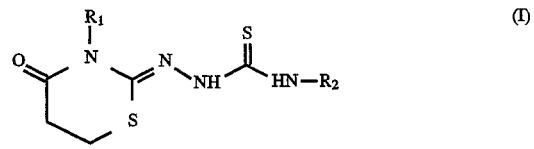

7 Claims, No Drawings

SUBSTITUTED THIOSEMICARBAZONE DERIVATIVES

The present invention relates to novel substituted thiosemicarbazone derivatives of formula I

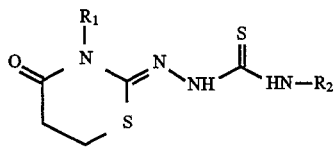

wherein $R_1$ is lower alkyl, lower alk-2-en-1-yl, lower alk-2-yn-1-yl, or aryl-lower alkyl, $R_2$ is hydrogen, lower alkyl, aryl, aryl-lower alkyl, lower alk-2-en-1-yl, lower alk-2-yn-1-yl, unsaturated or saturated heterocyclyl-lower alkyl, lower alkoxycarbonyl-lower alkyl or the group —C(=O)—$R_3$, wherein $R_3$ is lower alkyl, aryl, aryl-lower alkyl, aryl-lower alkenyl, heteroaryl (hetaryl), aryloxy, aryl-lower alkoxy or lower alk-2-en-1-yloxy, and the salts thereof, to a process for the preparation of said compounds, to pharmaceutical compositions containing them, and to the use thereof as medicaments.

Although some of the compounds falling under formula I above are already disclosed in DE-OS-2 632 747 as starting compounds for the preparation of azines from 6-membered thiaza heterocycles of formula II in DE-OS-2 632 747, no single compound is characterised by physical data or even specifically mentioned in an Example, so that none of the compounds embraced by formula I above may be claimed as known. The compounds embraced by general formula II of DE-OS-2 632 747 have not been prepared with the substituents named herein and are simply mentioned as starting compounds without any particulars whatever relating to pharmacological activity.

In this specification, radicals and compounds qualified by the term "lower" will be taken to mean those containing preferably up to and including 7, preferably up to and including 4, carbon atoms.

Lower alk-2-en-1-yl will typically be $C_3$–$C_5$alk-2-en-1-yl, preferably allyl or methallyl.

Lower alk-2-yn-1-yl will typically be $C_3$–$C_5$alk-2-yn-1-yl, preferably prop-2-yn-1-yl or also but-2-yn-1-yl.

Lower alkyl is $C_1$–$C_4$alkyl, typically methyl, ethyl, propyl or butyl.

Lower alkoxy is typically n-propoxy, isopropoxy, n-butoxy or tert-butoxy, preferably ethoxy and, most preferably, methoxy.

Aryl by itself and as moiety of composite radicals such as aryl-lower alkyl is typically phenyl or naphthyl, for example 1- or 2-naphthyl, or substituted phenyl or naphthyl, typically phenyl or naphthyl which are substituted by lower alkyl, hydroxy-lower alkyl, halo-lower alkyl, hydroxy, lower alkoxy, lower alkanoyloxy, halogen, cyano and/or nitro. Aryl is preferably unsubstituted phenyl or phenyl which is substituted as indicated above, and is most preferably phenyl.

Aryl-lower alkyl is preferably phenyl-lower alkyl and, most preferably, benzyl.

Lower alkoxycarbonyl-lower alkyl will typically be methoxy- or ethoxycarbonylmethyl or also methoxy- or ethoxycarbonylethyl.

Lower alkanoyloxy is typically propionyloxy or pivaloyloxy, and is preferably acetoxy.

Hydroxy-lower alkyl will typically be 2- or 3-hydroxy-lower alkyl such as 2-hydroxypropyl, 3-hydroxypropyl or 3-hydroxy-2-methylpropyl.

Halogen will be taken to mean halogen having an atomic number of up to and including 35, typically chloro or fluoro, and also bromo.

Halogen-lower alkyl will typically be 2- or 3-halo-lower alkyl such as 2-halopropyl, 3-halopropyl or 3-halo-2-methylpropyl.

Unsaturated heterocyclyl-lower alkyl is typically heteroaryl-lower alkyl (hetaryl-lower alkyl).

Hetaryl in composite radicals such as hetaryl-lower alkyl is preferably a monocyclic and also bicyclic or polycyclic heterocyclic radical having aromaticity. Bicyclic and polycyclic heteroaryl may be comprised of a plurality of heterocyclic rings or, preferably, may consist of one heterocycle and one or more than one, conveniently one or two and preferably one, fused carbocyclic ring, preferably a benzene ring. Each individual ring typically contains 3, 5, 6 or 7 ring members and, preferably, 5 or 6 ring members. Heteroaryl is preferably an azacyclic, thiacyclic, oxacyclic, thiazacyclic, thiadiazacyclic, oxazacyclic, dimcyclic, triazacyclic and tetrazacyclic radical.

Hetaryl is most preferably monocyclic monoazacyclic, monothiacyclic or monooxacyclic radicals such as pyrryl, e.g. 2-pyrryl or 3-pyrryl, pyridyl, e.g. 2-, 3- or 4-pyridyl, thienyl, e.g. 2- or 3-thienyl, or furyl, e.g. 2-furyl; bicyclic monoazacyclic, monooxacyclic or monothiacyclic radicals such as indolyl, e.g. 2- or 3-indolyl, quinolinyl, e.g. 2- or 4-quinolinyl, isoquinolinyl, e.g. 1-isoquinolinyl, benzofuranyl, e.g. 2- or 3-benzofuranyl, or benzothienyl, e.g. 2- or 3-benzothienyl; monocyclic diazacyclic, triazacyclic, tetrazacyclic, oxazacyclic, thiazacyclic or thiadiazacyclic radicals such as imidazolyl, e.g. 2-imidazolyl, pyrimidinyl, e.g. 2- or 4-pyrimidinyl, triazolyl, e.g. 1,2,4-triazol-3-yl, tetrazolyl, e.g. 1- or 5-tetrazolyl, oxazolyl, e.g. 2-oxazolyl, isoxazolyl, e.g. 3- or 4-isoxazolyl, thiazolyl, e.g. 2-thiazolyl, isothiazolyl, e.g. 3- or 4-isothiazolyl or 1,2,4- or 1,3,4-thiadiazolyl, e.g. 1,2,4-thiadiazol-3-yl or 1,3,4-thiadiazol-2-yl; or bicyclic diazacyclic, oxazacyclic or thiazacyclic radicals such as benzimidazolyl, e.g. benzimidazolyl, benzoxazolyl, e.g. 2-benzoxazolyl, or benzothiazolyl, e.g. 2-benzothiazolyl.

Hetaryl radicals are unsubstimted or they carry substituents. Suitable substiuents at the ring carbon atoms are conveniently those named above in connection with the aryl radicals and, additionally, oxo (=O). Ring nitrogen atoms may be substituted by lower alkyl, aryl-lower alkyl, lower alkanoyl, benzoyl, carboxy, lower alkoxycarbonyl, hydroxy, lower alkoxy, lower alkanoyloxy or oxido -$\bar{\text{O}}$|.

Hetaryl is most preferably pyridyl, thienyl, pyrryl or furyl.

Hetaryl-lower alkyl is most preferably pyridylmethyl, thienylmethyl, pyrrylmethyl or furylmethyl.

Saturated heterocyclyl-lower alkyl contains a 5- or 6-membered saturated heterocyclic ring which carries a nitrogen or oxygen atom and is preferably an azacyclic or oxacyclic radical which may be substituted or unsubstituted.

A saturated 6-membered heterocyclic ring may contain a nitrogen atom in addition to an oxygen atom.

A saturated 5- or 6-membered heterocyclic radical is conveniently pyrrolidinyl, pipefidino, piperidyl, tetrahydrofuranyl or tetrahydropyranyl, wherein one or also more than one hydrogen atom may be replaced by one or more than one substituent, typically by lower alkyl.

A saturated 6-membered heterocyclic radical which also contains a nitrogen atom in addition to an oxygen atom is typically morpholino or also morpholinyl.

Saturated heterocyclyl-lower alkyl is most preferably pyrrolidinylmethyl, tetrahydrofuranylmethyl or also tetrahydropyranylmethyl.

Pharmaceutically acceptable acid addition salts of compounds of formula I are typically their pharmaceutically acceptable salts with suitable mineral acids such as hydrohalic acids, sulfufic acid or phosphoric acid, including hydrochlorides, hydrobromides, sulfates, hydrogensulfates or phosphates, salts with suitable aliphatic or aromatic sulfonic acids or N-substituted sulfamic acids, including methanesulfonates, benzenesulfonates, p-tosylates or N-cyclohexylsulfamates (cyclamates), or salts with strong organic carboxylic acids such as lower alkanecarboxylic acids or unsaturated or hydroxylfited aliphatic dicarboxylic acids, including acetates, oxalates, malonates, maleates, fumarates, tartrates or citrates. Salts of compounds of formula I are typically acid addition salts, conveniently theft pharmaceutically acceptable salts with suitable mineral acids such as hydrohalic acids. sulfuric acid or phosphoric acid, including hydrochlorides, hydrobromides, sulfates, hydrogensulfates or phosphates, salts with suitable aliphatic or aromatic sulfonic acids or N-substituted sulfamic acids, including methanesulfonates, benzenesulfonates, p-tosylates or N-cyclohexylsulfamates (cyclamates).

The compounds of formula I and their pharmaceutically acceptable salts have valuable pharmacological properties. In particular, they have pronounced antiarthritic properties. These properties can be demonstrated in vivo in the adjuvans arthritis model in rats in accordance with the assay of L Wiesenberg et at. Clin. Exp. Immunol. 78, 245 (1989) in the dosage range from about 0.1 to about 10.0 mg/kg p.o. or i.p., preferably from about 0.1 to about 3.0 mg/kg p.o. or i.p.

The compounds of formula I and their pharmaceutically acceptable salts can therefore be used for treating diseases of rheumatoid genesis. Such diseases include in particular rheumatoid arthritis, juvenile arthritis, ankylosing spondylitis and other seronegative spondylarthrides, e.g. spondylarthritides in ulcerative colitis and Crohn's disease, and also reactive arthritides, collagen diseases such as lupus erythematosus, degenerative rheumatic diseases, extraarficular rheumatic and pararheumatic diseases such as gout and osteoporosis.

The invention relates in particular to compounds of formula I, wherein $R_1$ is $C_1$–$C_4$alkyl, $C_3$–$C_5$alk-2-en-1-yl, $C_3$–$C_5$alk-2-yn-1-yl, or phenyl-lower alkyl, $R_2$ is hydrogen, $C_1$–$C_4$alkyl, $C_3$–$C_5$alk-2-en-1-yl, $C_3$–$C_5$alk-2-yn-1-yl, phenyl, naphthyl, phenyl-lower alkyl, pyridyl-lower alkyl, thienyl-lower alkyl, pyrryl-lower alkyl or furyl-lower alkyl, pyrrolidinyl-lower alkyl, tetrahydrofuranyl-lower alkyl or tetrahydropyranyl-lower alkyl, or $C_1$–$C_4$-alkoxycarbonyl-$C_1$–$C_4$alkyl or the group —C(C=O)—$R_3$, wherein $R_3$ is $C_1$–$C_4$alkyl, phenyl, naphthyl, pyridyl, thienyl, pyrryl, furyl, phenoxy, phenyl-$C_1$–$C_4$alkoxy or $C_3$–$C_5$alk-2-en-1-yloxy, phenyl-lower alkyl or phenyl-lower alkylenyl, and the salts, preferably the pharmaceutically acceptable salts, thereof.

More particularly, the invention relates to compounds of formula I, wherein $R_1$ is $C_1$–$C_4$alkyl, typically methyl or ethyl, preferably propyl, $C_3$–$C_5$alk-2-en-1-yl such as allyl or methallyl, $C_3$–$C_5$alk-2-yn-1-yl such as prop-2-yn-1-yl, or phenyl-lower alkyl such as benzyl or phenylethyl, and $R_2$ is hydrogen, $C_1$–$C_4$alkyl such as methyl or ethyl, $C_3$–$C_5$alk-2-en-1-yl, typically allyl or methallyl, $C_3$–$C_5$alk-2-yn-1-yl such as prop-2-yn-1-yl, phenyl, phenyl-lower alkyl such as benzyl or phenethyl, pyridyl-lower alkyl, thienyl-lower alkyl, pyrryl-lower alkyl or furyl-lower alkyl, pyrrolidinyl-lower alkyl, tetrahydrofuranyl-lower alkyl or tetrahydropyranyl-lower alkyl, for example pyridylmethyl, thienylmethyl, pyrrylmethyl, or furylmethyl, pyrrolidinylmethyl, tetrahydrofuranylmethyl or tetrahydropyranylmethyl, $C_1$–$C_4$alkoxycarbonyl-$C_1$–$C_4$alkyl such as methoxy- or ethoxycarbonylmethyl or methoxy- or ethoxycarbonylethyl or the group —(=O)—$R_3$, wherein $R_3$ is $C_1$–$C_4$alkyl such as methyl, phenyl, pyridyl, thienyl, phenoxy, benzoxy, $C_3$–$C_5$alk-2-en-1-yloxy such as allyl or methallyloxy or also benzyl or phenylallyl, and the salts, preferably the pharmaceutically acceptable salts, thereof.

The invention relates very particularly to compounds of formula I, wherein $R_1$ is propyl, allyl, methallyl, prop-2-yn-1-yl or benzyl, and $R_2$ is hydrogen, methyl, allyl, prop-2-yn-1-yl, phenyl, benzyl, pyridylmethyl, thienylmethyl, pyrrylmethyl or furylmethyl, pyrrolidinylmethyl, tetrahydrofuranylmethyl or tetrahydropyranylmethyl or the group —C(=O)—$R_3$, wherein $R_3$ is methyl phenyl, phenoxy, benzoxy, allyloxy, benzyl or phenylallyl, and the salts, preferably the pharmaceutically acceptable salts, thereof.

The invention relates specifically to the compounds of formula I and the salts, preferably the pharmaceutically acceptable salts, thereof, named in the Examples.

The compounds of formula I can be prepared in a manner known per se by reacting a compound of formula II

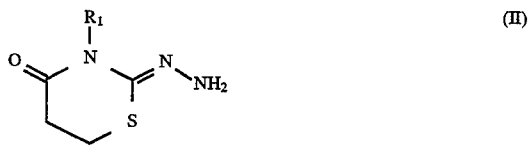

wherein $R_1$ is as defined above, with an isothiocyanate of formula III

The reaction of the hydrazone of general formula II with an isothiocyanate of general formula III is preferably carded out in an inert solvent, typically in a lower alkanol such as methanol, ethanol, propanol or isopropanol, an ethereal solvent such as diethyl ether, dibutyl ether, tetrahydrofuran or dioxane, a hydrocarbon such as benzene, toluene or hexane, or a halogenated hydrocarbon such as chloroform, at room temperature or at moderately elevated temperature up to c. 100° or the boiling temperature of the solvent employed. Depending on the reaction temperature and the reactivity of the starting materials, the reaction time is from about half an hour to 24 hours.

Starting materials of general formula H are novel and can be obtained from compounds of general formula IV

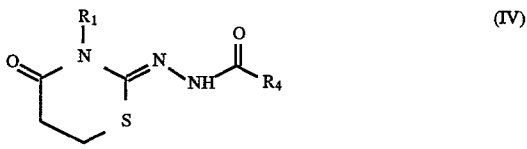

wherein $R_1$ is as defined above and $R_4$ is a lower alkyl or aryl-lower alkyl radical, preferably methyl or benzyl, by treatment with a mineral acid, preferably hydrochloric acid.

The reaction is carried out in an anhydrous inert solvent as already noted above in connection with the reaction of compounds of formula II with compounds of formula III, preferably in an anhydrous lower alkanol, conveniently in an anhydrous mixture of methanol and ethanol at room temperature, to give a salt, e.g. the hydrochloride, of a compound of general formula II, which salt can be converted into the free hydrazine by addition of a base, conveniently a solution of an alkali metal carbonate or alkaline earth metal carbonate, preferably a solution of sodium carbonate.

Compounds of general formula IV can in turn be obtained by alkylating a compound of general formula V

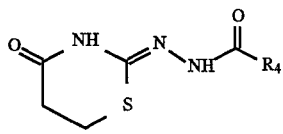

wherein R₄ is as defined for formula IV, with the corresponding halide of formula VI

R₁—X (VI)

wherein R₁ is as defined for formula I, and X is a halogen atom, preferably a bromine atom. The alkylation is carried out in an inert solvent, preferably dimethyl formamide (DMF), in the presence of a strong base, conveniently potassium tert-butylate, sodium hydride, sodium amide or also lithium diisopropylamide (LDA), to give a mixture of the N-alkylamide of general formula IV and the O-alkylated imino ether of general formula VII

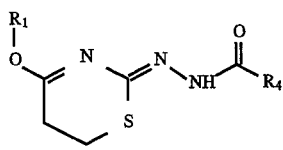

wherein R₁ and R₄ are as defined for formula IV, in a specific ratio. The separation of the resultant compound of general formula IV from the compound of general formula VII can be effected by fractional crystallisation and/or by chromatography.

Compounds of general formula V can be prepared by cyclising the known compounds of general formula VIII

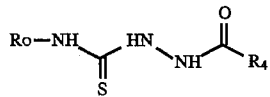

wherein R₀ is an acryloyl group (vinylcarbonyl group) or a radical that is convertible into an acryloyl group, e.g. 3-chloropropionyl, and R₄ is as defined for formula IV.

The cyclisation is carried out by gentle heating in an inert solvent as already noted above in connection with the reaction of compounds of formula II with compounds of formula III, preferably in a lower alkanol such as ethanol or also in acetonitrile.

The isothiocyanates of formula III can usually be prepared from the corresponding amines of formula IX

R₂—NH₂ (IX)

wherein R₂ is as defined above, by treatment with thiophosgene.

Compounds of formula I can be prepared by a further process b) by reacting compounds of formula X

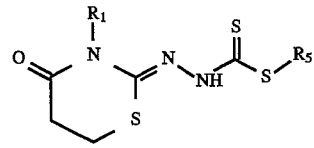

wherein R₁ is as defined above and R₅ is a lower alkyl radical, with corresponding amines mentioned above of formula IX

R₂—NH₂ (IX)

wherein R₂ is as defined above.

The condensation of the compounds of formula X with the compounds of formula IX is carried out in known manner in a protic or aprotic solvent, conveniently in an aliphatic halogenated hydrocarbon, as in dichloromethane, preferably methylene chloride, or in an aliphatic or cycloaliphatic ether, e.g. in tetrahydrofuran or also dioxane. Illustrative examples of further suitable solvents are acetonitrile, ethanol and toluene.

The compounds are reacted in the temperature range from 25° to 120° C., conveniently at the boiling temperature of the solvent in the presence of a basic condensing agent, typically dimethylaminopyridine, a tri-lower alkylamine such as triethylamine, or also quinoline or pyridine.

The starting compounds of formula X are novel and can be prepared from the corresponding aforementioned hydrazone of formula II by reaction with carbon disulfide (CS₂) and subsequent reaction with a lower alkyl iodide. The reaction of a compound of formula II with carbon disulfide is carried out in the presence of a tertiary organic base, e.g. a tri-lower alkylamine, a Hüilnig base or an organic nitrogen base such as pyridine or quinoline. The subsequent reaction with a lower alkyl iodide is carried out by cooling the reaction mixture to a temperature from −10° to +10° C., preferably from 0° to +5° C.

Resultant salts can be converted in per se known manner in the free compounds, conveniently by treatment with a base such as an alkali metal hydroxide, a metal carbonate or metal hydrogen carbonate or ammonia, or with another salt-forming base mentioned at the outset or with an acid, conveniently a mineral acid such as hydrochloric acid, or with another salt-forming acid mentioned at the outset.

Resultant salts can be converted in a manner known per se into other salts, acid addition salts conveniently by treatment with a suitable metal salt, typically a sodium, barium or silver salt, of another acid in a suitable solvent in which a resultant inorganic salt is insoluble and is thus eliminated from the equilibrium of reaction, and salts of bases by generating the free acid and repeated salt-formation.

The compounds of formula I, including their salts, may also be obtained in the form of hydrates or include the solvent used for crystallisation.

Because of the close relationship between the novel compounds in the free form and in the form of their salts, the references made throughout this specification to the free compounds and their salts will also apply by analogy to the corresponding salts and free compounds.

Racemates can also be separated by known methods into the optical antipodes, conveniently by recrystallisation from an optically active solvent, with the aid of microorganisms or by reacting the mixture of diastereoisomers or racemate with an optically active compound, e.g. depending on the acid, basic or functionally modifiable groups present in the compound of formula I, with an optically active acid, base or an optically active alcohol, into mixtures of diastereoisomeric salts or functional derivatives such as esters, separating said mixtures into the diastereoisomers from which each desired enantiomer can be set free in the customary manner. Bases, acids or alcohols suitable for the purpose are typically optically active alkaloid bases such as strychine, cinchonine or brucine, or D- or L-(1-phenyl)ethylamine, 3-pipecoline, ephedrine, amphetamine or similar bases which are obtainable by synthesis, optically active carboxylic or sulfonic acids such as quinic acid or D- or L-tartaric acid, D- or L-di-o-toluyltartaric acid, D- or L-malic acid, D- or L-mandelic acid or D- or L-camphorsuffonic acid, or optically active alcohols such as borneol or D- or L-(1-phenyl)ethanol.

The invention relates also to those embodiments of the process in which a compound obtainable as intermediate in any stage of the process is used as starting material and the remaining steps are carried out, or a starting material is used in the form of a salt or, preferably, is formed under the reaction conditions.

The invention also relates to the novel starting materials which have been specially developed for the preparation of the novel compounds, especially those which result in the compounds of formula I described at the beginning as being especially preferred, to processes for their preparation and to the use thereof as intermediates.

The pharmaceutical compositions of this invention which contain the novel compound, or a pharmaceutically acceptable salt thereof, are those for enteral, e.g. oral, and also rectal and parenteral administration to warm-blooded animals, and they contain the pharmacologically active compound alone or together with a pharmaceutically acceptable carrier. The daily dose will depend on the age, sex and individual condition of the patient as well as on the mode of administration.

The novel pharmaceutical compositions contain from about 10 to 80%, preferably from about 20 to 60%, of the active compound. Pharmaceutical compositions for enteral or parenteral administration are typically those in dosage unit forms such as dragée, tablets, capsules or suppositories, and also ampoules. These dosage forms are prepared in a manner known per se, typically by conventional mixing, granulating, confectioning, dissolving or lyophilising methods. Pharmaceutical compositions for oral administration can typically be prepared by combining the the active compound with solid carriers, granulating the mixture so obtained and, if desired or necessary, processing the mixture or granulate, after addition of suitable excipients, to tablets or dragée cores.

Suitable carriers are especially fillers such as sugars, conveniently lactose, saccharose, mannitol or sorbitol, cellulose preparations and/or calcium phosphates, typically tricalcium phosphate or calcium hydrogen phosphate, and also binders such as starch pastes, conveniently using maize, corn, rice or potato starch, gelatin, tragacanth, methyl cellulose and/or polyvinyl pyrrolidone, and/or, if desired, disintegrators such as the above-mentioned starches, also carboxymethyl starch, crosslinked polyvinylpyrrolidone, agar, alginic acid or a salt thereof such as sodium alginate. Excipients are in particular glidants, flow control agents and lubricants, conveniently silica, talcum, stearic acid or salts thereof, typically magnesium stearate or calcium stearate, and/or polyethylene glycol.

Dragée cores can be provided with suitable non-enteric or enteric coatings, typically using concentrated sugar solutions which may contain gum arabic, talcum, polyvinylpyrrolidone, polyethylene glycol and/or titanium dioxide, shellac solutions in suitable organic solvents or mixtures of solvents or, for the preparation of enteric coatings, solutions of suitable cellulose preparations such as acetyl cellulose phthalate or hydroxypropylmethyl cellulose phthalate. Dyes or pigments can be added to the tablets or dragée coatings, conveniently to identify or indicate different doses of active compound.

Further pharmaceutical compositions for oral administration are dry-filled capsules made of gelatin and also soft-sealed capsules consisting of gelatin and a plasticiser such as glycerol or sorbitol. The dry-filled capsules can contain the active ingredient in the form of granules, conveniently in admixture with fillers such as lactose, binders such as starches, and/or glidants such as talcum or magnesium stearate, and with or without stabilisers. In soft capsules, the active ingredient is preferably dissolved or suspended in a suitable liquid, typically a fatty oil, paraffin oil or a liquid polyethylene glycol, to which a stabiliser can also be added.

Suitable pharmaceutical compositions for rectal administration are typically suppositories, which consist of a combination of the active compound with a suppository base. Examples of suitable suppository bases are natural or synthetic triglycerides, paraffin hydrocarbons, polyethylene glycols and higher alkanols. It is also possible to use gelatin capsules for rectal administration that contain a combination of the active compound with a base substance. Suitable base substances are typically liquid triglycerides, polyethgylene glycol or paraffin hydrocarbons.

Most suitable for parenteral administration are aqueous solutions of an active compound in water-soluble form, for example of a water-soluble salt, and also suspensions of the active compound, conveniently oily injection suspensions using suitable lipophilic solvents or vehicles such as fatty oils, typically sesame oil, or synthetic fatty acid esters such as ethyl oleate or triglycefides, or aqueous injection suspensions which may contain viscosity increasing substances, conveniently sodium carboxymethyl cellulose, sorbitol and/or dextran, and also with or without stabilisers.

The invention also relates to the use of the compounds of formula I, preferably in the form of pharmaceutical compositions. The dosage of the active compound will depend on the species of the warm-blooded animal, on the age and individual condition of the patient, and also on the mode of administration. The contemplated daily dosage for oral administration to a patient of approximately 75 kg body weight will normally be from about 5 mg to 1000 mg, preferably from about 10 mg to 200 mg. This dose can be administered in a single dose or in several, typically from 2 to 4, individual doses. Pharmaceutical compositions in dosage unit form thus contain from about 5 mg to 250 mg, preferably from about 10 mg to 50 mg, of active compound.

The invention is illustrated in more detail by the following non-limitative Examples. Pressures are given in mbar.

EXAMPLE 1

With stirring, 0.5 g of (3-allyl-4-oxo-[1,3]thiazinan-2-ylidene) hydrazone and 0.2 g of methyl isothiocyanate are refluxed in 5 ml of ethanol as solvent for 1 hour. After cooling to room temperature, the product is crystallised by addition of ether. The product is isolated by filtration, washed with petroleum ether and dried under vacuum, giving the solid 1-(3-ally-4-oxo-[1,3]thiazinan-2-ylidene)-4-methylthiosemicarbazone; m.p. 127°–128° C.

$^1$H-NMR: 3.0 (m, 2H), 3.15 (m, 2H), 3.2 (d, 3H), 4.6 (d, 2H), 5.1–5.25 (m, 2H), 5.75–5.9 (m, 1H), 7.0 (br. s, 1H), 8.1 (br. s, 1H).

EXAMPLE 2

In general accordance with the procedure described in Example 1, 0.25 g of (3-allyl-4-oxo-[1,3]thiazinan-2-ylidene) hydrazone and 0.2 g of phenyl isothiocyanate are stirred in 3 ml of ethanol for 1 hour at room temperature. The product is isolated by filtration, washed with petroleum ether and dried under vacuum, giving the solid 1-(3-all-yl-4-oxo-[1,3]thiazinan-2-ylidene)-4-phenylthiosemicarbazone; m.p. 150°–151° C.

$^1$H-NMR: 3.05 (m, 2H), 3.2 (m, 2H), 4.65 (d, 2H), 5.2–5.3 (m, 2H), 5.8–5.95 (m, 1H), 7.2 (t, 1H), 7.4 (t, 2H), 7.6 (d, 2H), 8.2 (br. s, 1H), 8.75 (br. s, 1H).

EXAMPLE 3

In general accordance with the procedure described in Example 1, 0.3 g of (3-allyl-4-oxo-[1,3]thiazinan-2-ylidene) hydrazone and 0.6 g of furan-2-methylisothiocyanate are refluxed for 1 hour in 5 ml of ethanol, with stirring. The solvent is stripped off on a rotary evaporator and the residue is chromatographed on silica gel with methylene chloride as eluant. The product is crystallised from ethanol/ether and collected by filtration to give the solid 1-(3-allyl-4-oxo-[1,3]thiazinan-2-ylidene)-4-(furan-2-methyl)-thiosemicarbazone; m.p. 88°–89° C.

$^1$H-NMR: 3.0 (m, 2H), 3.15 (m, 2H), 4.55 (d, 2H), 4.8 (d, 2H), 5.0–5.1 (m, 2H), 5.7–5.8 (m, 1H), 6.35 (m, 2H), 7.2 (br. s, 1H), 7.4 (s, 1H), 8.1 (br. s, 1H).

EXAMPLE 4

In general accordance with the procedure described in Example 1, 0.4 g of (3-allyl-4-oxo-[1,3]thiazinan-2-ylidene) hydrazone and 0.6 g of thiophene-2-methylisothiocyanate are refluxed in 5 ml of ethanol for 0.75 hour, with stirring. The solvent is stripped off on a rotary evaporator and the residue is chromatographed on silica gel with methylene chloride as eluant. The product is crystallised from ethanol/ether and collected by filtration to give the solid 1-(3-allyl-4-oxo-[1,3]thiazinan-2-ylidene)-4-(thiophene-2-methyl) thiosemicarbazone; m.p. 80° C.

$^1$H-NMR: 3.0 (m, 2H), 3.15 (m, 2H), 4.9-5.1 (m, 4H), 5.65–5.8 (m, 1H), 6.95 (m, 1H), 7.05 (d, 1 H), 7.15 (br. s, 1H), 7.3 (d, 1H), 8.1 (br. s, 1H).

EXAMPLE 5

In general accordance with the procedure described in Example 1, 0.5 g of (3-allyl-4-oxo-[1,3]thiazinan-2-ylidene) hydrazone and 0.9 g of tetrahydrofuran-2-methyl-isothiocyanate are refluxed in 5 ml of ethanol for 1.5 hours, with stirring. The solvent is stripped off on a rotary evaporator and the residue is chromatographed on silica gel with methylene chloride. The product is crystallised from ethanol/ether and collected by filtration to give the solid 1-(3-allyl-4-oxo-[1,3]thiazinan-2-ylidene)-4-(tetrahydrofuran-2-methyl)thiosemicarbazone; m.p. 98° C. 1H-NMR: 1.6 (m, 1H), 1.85–2.1 (m, 3H), 3.0 (m, 2H), 3.15 (m, 2H), 3.6 (m, 1H), 3.75 (m, 1H), 3.85 (m, 1H), 3.95–4.1 (m, 2H), 4.6 (d, 2H), 5.15–5.3 (m, 2H), 5.75–5.9 (m, 1H), 7.4 (br. s, 1H), 8.05 (br. s, 1H).

EXAMPLE 6

In general accordance with the procedure described in Example 1, 0.5 g of (3-allyl-4-oxo-[1,3]thiazinan-2-ylidene) hydrazone and 0.45 g of glycine ethylisothiocyanate are refluxed in 5 ml of ethanol for 1 hour, with stirring. The solvent is stripped off on a rotary evaporator and the residue is chromatographed on silica gel with methylene chloride. The product is crystallised from ethanol/ether and collected by filtration to give the solid 1-(3-allyl-4-oxo-[1,3]thiazinan-2-ylidene)-4-(l-ethoxy-2-acetyl)thiosemicarbazone; m.p. 105°–106° C.

$^1$H-NMR: 1.3 (t, 3H), 3.0 (m, 2H), 3.15 (m, 2H), 4.25 (q, 2H), 4.4 (d, 2H), 4.65 (d, 2H), 5.2–5.3 (m, 2H), 5.8–5.9 (m, 1H), 7.5 (br. s, 1H), 8.2 (br. s, 1H).

EXAMPLE 7

In general accordance with the procedure described in Example 1, 0.3 g of (3-allyl-4-oxo-[1,3]thiazinan-2-ylidene) hydrazone and 0.17 g of allyl isothiocyanate are refluxed in 10 ml of ethanol for 1 hour, with stirring. The solvent is stripped off on a rotary evaporator and the residue is crystallised from a small amount of methylene chloride/ether. The crystalline product is collected by filtration to give the solid 1-(3-allyl-4-oxo-[1,3]thiazinan-2-ylidene)-4-allylthiosemicarbazone; m.p. 76°–77° C.

$^1$H-NMR: 3.0 (m, 2H), 3.15 (m, 2H), 4.3 (m, 2H), 4.6 (d, 2H), 5.1–5.3 (m, 4H), 5.75–6.0 (m, 2H), 7.0 (br. s, 1H), 8.1 (br. s, 1H).

EXAMPLE 8

In general accordance with the procedure described in Example 1, 0.2 g of (3-allyl-4-oxo-[1,3]thiazinan-2-ylidene) hydrazone and 0.25 g of p-bromophenyl isothiocyanate are stirred in 5 ml of ethanol for 1 hour at room temperature. The precipitated product is collected by filtration, washed with petroleum ether and dried, giving the solid 1-(3-allyl-4-oxo-[1,3]thiazinan-2-ylidene)-4-(p-bromophenyl) thiosemicarbazone; m.p. 168°–170° C.

$^1$H-NMR: 3.05 (m, 2H), 3.2 (m, 2H), 4.65 (d, 2H), 5.2–5.3 (m, 2H), 5.8–5.95 (m, 1H), 7.5 (m, 4H), 8.25 (br. s, 1H), 8.7 (br. s, 1H).

EXAMPLE 9

0.5 g of (3-allyl-4-oxo-[1,3]thiazinan-2-ylidene)-hydrazono-1-dithioformic acid methyl ester amide and 0.18 g of propargylamine hydrochloride are refluxed in the presence of 0.27 ml of triethylamine and a catalytic amount of dimethylaminopyridine in 10 ml of ethanol for 2.5 hours. The solvent is stripped of on a rotatary evaporator and the residue is chromatographed on silica gel with methylene chloride. After crystallisation from ethanol/ether, the crystalline product is collected by filtration to give the solid 1-(3-allyl-4-oxo-[1,3]thiazinan-2-ylidene)-4-(propynyl) thiosemicarbazone; m.p. 117°–118° C.

$^1$H-NMR: 2.3 (s, 1H), 3.05 (m, 2H), 3.15 (m, 2H), 4.45 (m, 2H), 4.6 (d, 2H), 5.2 (m, 2H), 5.75–5.9 (m, 1H), 7.05 (br. s, 1H), 8.1 (br. s, 1H).

EXAMPLE 10

In accordance with the general procedure described in Example 1, 0.48 g of (3-propynyl-4-oxo-[1,3]thiazinan-2-ylidene) hydrazone and 0.2 g of methyl isothiocyanate are refluxed in 15 ml of ethanol for 1 hour, with stirring. Two-thirds of the solvent are stripped off on a rotary evaporator and the residue is left to stand over night at 0° C. The precipitated product is isolated by filtration, washed with petroleum ether and dried, giving the solid 1-(3-propynyl-4-oxo-[1,3]thiazinan-2-yliden)-4-methylthiosemicarbazone; m.p. 165° C.

$^1$H-NMR: 2.25 (s, 1H), 3.05 (m, 2H), 3.15 (m, 2H), 3.25 (d, 3H), 4.7 (s, 2H), 7.3 (br. s, 1H), 8.1 (br. s, 1H).

EXAMPLE 11

In accordance with the general procedure described in Example 1, 0.2 g of (3-propyl-4-oxo-[1,3]thiazinan-2-ylidene) hydrazone and 0.08 g of methyl isothiocyanate are refluxed in 3 ml of ethanol for 1.5 hours, with stirring. After cooling to room temperature, the product is crystallised by addition of ether and petroleum ether. The product is isolated by filtration, washed with petroleum ether and dried under vacuum, giving the solid 1-(3-propyl-4-oxo-[1,3]thiazinan-2-ylidene)-4-methylthiosemicarbazone; m.p. 118°–119° C.

$^1$H-NMR: 0.9 (t, 3H), 1.55–1.7 (m, 2H), 2.95 (m, 2H), 3.1 (m, 2H), 3.2 (d, 3H), 3.95 (m, 2H), 6.95 (br. s, 1H), 8.1 (br. s, 1H).

EXAMPLE 12

In accordance with the general procedure described in Example 1, 0.15 g of (3-methallyl-4-oxo-[1,3]thiazinan-2-ylidene) hydrazone and 0.06 g of methyl isothiocyanate are refluxed in 2 ml of ethanol for 2 hours, with stirring. After cooling to room temperature, the product is crystallised by addition of ether. The product is isolated by filtration, washed with petroleum ether and dried under vacuum, giving the solid 1-(3-methallyl-4-oxo-[1,3]thiazinan-2-ylidene)-4-methylthiosemicarbazone; m.p. 130°–131° C.

$^1$H-NMR: 1.7 (s, 3H), 3.0 (m, 2H), 3.15 (m, 2H), 4.55 (s, 2H), 4.7 (s, 1H), 4.85 (s, 1H), 7.0 (br. s, 1H), 8.05 (br. s, 1H).

EXAMPLE 13

In accordance with the general procedure described in Example 1, 0.25 g of (3-allyl-4-oxo-[1,3]thiazinan-2-ylidene) hydrazone and 0.2 g of benzoyl isothiocyanate are stirred in 15 ml of ethanol for 1.5 hours at room temperature. Two-thirds of the solvent are stripped off on a rotary evaporator. The precipitated product is isolated by filtration, washed with petroleum ether and dried, giving the solid 1-(3-allyl-4-oxo-[1,3]thiazinan-2-ylidene)-4-methylthiosemicarbazone; m.p. 190° C.

$^1$H-NMR: 3.0 (m, 2H), 3.15 (m, 2H), 4.75 (s, 2H), 5.25 (d, 1H), 5.4 (d, 1H), 5.9–6.05 (m, 1H), 7.5 (m, 2H), 7.65 (m, 1H), 7.9 (d, 2H), 9.1 (br. s, 1H), 13.3 (br. s, 1H).

EXAMPLE 14

0.23 g of ammonium thiocyanate are dissolved in 20 ml of absolute acetonitrile. With stirring, 0.31 ml of isobutyryl chloride are added dropwise at 0° C. and the mixture is thereafter stirred for 0.5 hour at the same temperature. Then 0.5 g of (3-allyl-4-oxo-[1,3]thiazinan-2-ylidene) hydrazone in a small amount of acetonitrile is added dropwise and the mixture is subsequently warmed to room temperature and stirred for 1 hour. The suspension is diluted with water and the precipitated product is filtered. The residue is dissolved in methylene chloride, dried over sodium sulfate and the solvent is stripped off on a rotary evaporator. The residue is chromatographed on silica gel with the solvent system methylene chloride/acetone (c. 15:1). The product is recrystallised from methylene chloride/ether and the crystalline product is collected by filtration, washed with petroleum ether and dried, giving the solid 1-(3-allyl-4-oxo-[1,3]thiazinan-2-ylidene)-4-(2-methylpropionyl)thiosemicarbazone; m.p. 168°–69° C.

$^1$H-NMR: 1.25 (d, 6H), 2.55 (m, 1H), 3.0 (m, 2H), 3.15 (m, 2H), 4.75 (d, 2H), 5.2 (d, 1H), 5.4 (d, 1H), 5.9–6.05 (m, 1H), 8.9 (br. s, 1H), 13.0 (br. s, 1H)

EXAMPLE 15

In accordance with the general procedure described in Example 14, 0.23 g of ammonium thiocyanate are dissolved in 20 ml of absolute acetonitrile. With stirring, 0.38 ml of phenyl chloroformate are added dropwise at room temperature and the mixture is then stirred for 1 hour at the same temperature. Then 0.5 g of (3-allyl-4-oxo-[1,3]thiazinan-2-ylidene) hydrazone in a small amount of acetonitrile is added dropwise and thereafter the mixture is warmed to room temperature and stirred for 1 hour. The suspension is diluted with water and the precipitated product is filtered. The residue is dissolved in methylene chloride, dried over sodium sulfate and the solvent is stripped off on a rotary evaporator. The product is recrystallised from methylene chloride/ether and the crystalline product is collected by filtration, washed with petroleum ether and dried, giving the solid 1-(3-allyl-4-oxo-[1,3]thiazinan-2-ylidene)-4-(phenoxycarbonyl)thiosemicarbazone; m.p. 156°–157° C.

$^1$H-NMR: 3.0 (m, 2H), 3.1 (m, 2H), 4.75 (d, 2H), 5.2 (d, 1H), 5.4 (d, 1H), 5.9–6.05 (m, 1H), 7.15 (d, 2H), 7.3 (m, 1H), 7.4 (t, 2H), 8.5 (br. s, 1H), 11.9 (br. s, 1H).

EXAMPLE 16

In accordance with the general procedure described in Example 14, 0.35 g of ammonium thiocyanate are dissolved in 20 ml of absolute acetonitrile. With stirring, 0.32 ml of acetyl chloride is added dropwise at 0° C. and the mixture is then stirred for 1 hour at the same temperature. Then 0.7 g of (3-allyl-4-oxo-[1,3]thiazinan-2-ylidene) hydrazone in a small amount of acetonitrile is added dropwise and thereafter the mixture is warmed to room temperature and stirred for 2 hours. The suspension is diluted with water and the precipitated by-product is removed by filtration. The mother liquor is diluted again with water and the precipitated product is collected by filtration. The second crystalline product from the mother liquor is washed with ethanol and dried, giving the solid 1-(3-allyl-4-oxo-[1,3]thiazinan-2-ylidene)-4-acetylthiosemicarbazone; m.p. 158°–160° C.

$^1$H-NMR: 2.2(s, 3H), 3.0(m, 2H), 3.15(m, 2H), 4.75(d, 2H), 5.2(d, 1H), 5.4(d, 1H) 5.9–6.05(m, 1H), 9.3(br.s, 1H), 13.0(br.s, 1H).

EXAMPLE 17

Tablets each containing 10 mg of active ingredient may be prepared as follows:

Composition (10 000 tablets)

| | |
|---|---|
| active ingredient | 100.0 g |
| lactose | 450.0 g |
| potato starch | 350.0 g |
| gelatin | 10.0 g |
| talcum | 60.0 g |
| magnesium stearate | 10.0 g |
| silica (highly dispersed) | 20.0 g |
| ethanol | q.s. |

The active ingredient is mixed with the lactose and 292 g of potato starch. The mixture is moistened with an ethanolic solution of gelatin and granulated through a sieve. The granulate is dried and the remainder of the potato starch, the talcum, the magnesium stearate and the silica are added and the mixture is compressed to 100.0 mg tablets each containing 10.0 mg of active ingredient. If desired, the tablets can be provided with a breaking notch for freer adjustment of the dose.

EXAMPLE 18

Hard gelatin capsules containing 20 mg of active ingredient may be prepared as follows:

Composition (for 1000 capsules)

| | |
|---|---|
| active ingredient | 20.0 g |
| lactose | 240.0 |
| microcrystalline cellulose | 30.0 g |
| sodium lauryl sulfate | 2.0 g |
| magnesium stearate | 8.0 g |

The sodium lauryl sulfate is sieved through a sieve having a mesh size of 0.2 mm and added to the lyophilised active ingredient and both components are thoroughly mixed. First the lactose is passed through a sieve having a mesh size of 0.6 mm and then the microcrystalline cellulose is passed through a sieve having a mesh size of 0.9 mm. The ingredients are then thoroughly mixed again for 10 minutes. Finally, the magneisum stearate is passed through a sieve having a mesh size of 0.8 min. After mixing for 3 minutes, size 0 hard gelatin capsules are each filled with 390 mg of the formulation so obtained.

EXAMPLE 19

Hard gelatin capsules containing 100 mg of active ingredient may be prepared as follows:

Composition (for 1000 capsules)

| active ingredient | 100.0 g |
|---|---|
| lactose | 250.0 |
| microcrystalline cellulose | 30.0 g |
| sodium lauryl sulfate | 2.0 g |
| magnesium stearate | 8.0 g |

The sodium lauryl sulfate is sieved through a sieve having a mesh size of 0.2 mm and added to the lyophilised active ingredient and both components are thoroughly mixed. First the lactose is passed through a sieve having a mesh size of 0.6 mm and then the microcrystalline cellulose is passed through a sieve having a mesh size of 0.9 mm. The ingredients are then thoroughly mixed again for 10 minutes. Finally, the magneisum stearate is passed through a sieve having a mesh size of 0.8 min. After mixing for 3 minutes, size 0 hard gelatin capsules are each filled with 390 mg of the formulation so obtained.

EXAMPLE 20

Film-coated tablets each containing 50 mg of active ingredient may be prepared as follows:

Composition (for 1000 film-coated tablets)

| active ingredient | 50.0 g |
|---|---|
| lactose | 100.0 g |
| corn starch | 70.0 g |
| talcum | 10.0 g |
| calcium stearate | 2.0 g |
| hydroxypropyl methyl cellulose | 2.36 g |
| shellac | 0.64 g |
| water | q.s. |
| methylene chloride | q.s. |

The active ingredient, the lactose and 40 g of corn starch are mixed and moistened with a paste prepared from 15 g of corn starch and water (with heating), and the mixture is granulated. The granulate is dried, the remainder of the corn starch, the talcum and the calcium stearate are added and mixed with the granulate. The mixture is compressed to 240 mg tablets which are coated with a solution of hydroxypropyl methyl cellulose and shellac in methylene chloride. Final weight of the tablets: 283 mg.

EXAMPLE 21

A 0.2 % injection or infusion solution of the active ingredient may be prepared as follows:

Composition (for 1000 ampoules)

| active ingredient | 5.0 g |
|---|---|
| sodium chloride | 22.5 g |
| phosphate buffer pH = 7.4 | 300.0 g |
| demineralised water | ad 2500.0 ml |

The active ingredient is dissolved in 1000 ml of water and filtered through a microfilter. The buffer solution is added, followed by the addition of water to make up 2500 ml. To prepare dosage unit forms, 1.0 or 2.5 ml of the asolution are filled into glass ampoules each containing 2.0 or 5.0 mg of active ingredient.

EXAMPLE 22

1% ointment (O/W emulsion), containing an active ingredient, of the following composition:

| active ingredient | 1.0 g |
|---|---|
| cetyl alcohol | 3.0 g |
| glycerol | 6.0 g |
| methyl parabene | 0.18 g |
| propyl parabene | 0.05 g |
| Arlacel 60 | 0.6 g |
| Tween 60 | 4.4 g |
| stearic acid | 9.0 g |
| isopropyl palmitate | 2.0 g |
| paraffin oil, viscous | 10.0 g |
| demin. water q.s. ad | 100.0 g |

EXAMPLE 23

1% gel, containing active ingredient, of the following composition:

| active ingredient | 1.0 g |
|---|---|
| Carbopol 934 P | 1.0 g |
| glycerol | 3.0 g |
| isopropanol | 25.0 g |
| Softigen ® 767 | 0.2 g |
| demin. water q.s. ad | 100.0 g. |

What is claimed is:

1. A compound of formula I

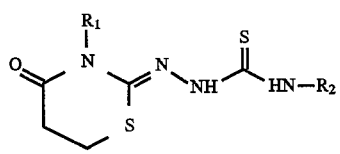

(I)

wherein $R_1$ is $C_1$–$C_4$ alkyl, $C_3$–$C_5$ alk-2-en-1-yl, $C_3$–$C_5$ alk-2-yn-1-yl, or phenyl-lower alkyl, $R_2$ is hydrogen, $C_1$–$C_4$alkyl, phenyl, naphthyl, phenyl-lower alkyl, $C_3$–$C_5$alk-2-en-1yl, $C_3$–$C_5$alk-2-yn-1-yl, pyridyl-lower alkyl, thienyl-lower alkyl, pyrryl-lower alkyl or furyl-lower alkyl, pyrrolidinyl-lower alkyl, tetrahydrofuranyl-lower alkyl or tetrahydropyranyl-lower alkyl, or $C_1$–$C_4$alkoxycarbonyl-$C_1$–$C_4$alkyl or the group —C(C═O)—$R_3$ wherein $R_3$ is $C_1$–$C_4$alkyl, phenyl, naphthyl, pyridyl, thienyl, pyrryl, furyl, phenoxy, phenyl-$C_1$–$C_4$ alkoxy or $C_3$–$C_5$alk-2-en-1-yloxy, phenyl-lower alkyl or phenyll-lower alkylenyl, or a pharmaceutically acceptable salt thereof.

2. A compound of formula I according to claim 1, wherein $R_1$ is $C_1$–$C_4$alkyl, typically methyl or ethyl, preferably propyl, $C_3$–$C_5$alk-2-en-1-yl such as allyl or methallyl, $C_3$–$C_5$alk-2-yn-1-yl such as prop-2-yn-1-yl, or phenyl-lower alkyl such as benzyl or phenylethyl, and $R_2$ is hydrogen, $C_1$–$C_4$alkyl such as methyl or ethyl, phenyl, phenyl-lower alkyl such as benzyl or phenethyl, $C_3$–$C_5$alk-2-en-1-yl, typically allyl or methallyl, $C_3$–$C_5$alk-2-yn-1-yl such as prop-2-yn-1-yl, phenyl, pyridyl-lower alkyl, thienyl-lower alkyl, pyrryl-lower alkyl or furyl-lower alkyl, pyrrolidinyl-lower alkyl, tetrahydrofuranyl-lower alkyl or tetrahydropyranyl-lower alkyl, for example pyridylmethyl, thienylmethyl, pyrrylmethyl, or furylmethyl, pyrrolidinylmethyl, tetrahydrofuranylmethyl or tetrahydropyranylmethyl, $C_1$–$C_4$alkoxycarbonyl-$C_1$–$C_4$alkyl such as methoxy- or ethoxycarbonylmethyl or methoxy- or ethoxycarbonylethyl or the group —C(=O)—$R_3$, wherein $R_3$ is $C_1$–$C_4$alkyl such as methyl, phenyl, pyridyl, thienyl, phenoxy, benzoxy, $C_3$–$C_5$alk-2-en-1-yloxy such as allyl or methallyloxy or also benzyl or phenylallyl, or a pharmaceutically acceptable salt thereof.

3. A compound of formula I according to claim 1, wherein $R_1$ is propyl, allyl, methallyl, prop-2-yn-1-yl or benzyl, and $R_2$ is hydrogen, methyl, phenyl, benzyl, allyl, prop-2-yn-1-yl, pyridylmethyl, thienylmethyl, pyrrylmethyl or furylmethyl, pyrrolidinylmethyl, tetrahydrofuranylmethyl or tetrahydropyranylmethyl or the group —C(=O)—$R_3$, wherein $R_3$ is methyl, phenyl, phenoxy, benzoxy, allyloxy, benzyl or phenylallyl, or a pharmaceutically acceptable salt thereof.

4. A process for the preparation of a novel compound of formula I according to claim 1, which comprises a) reacting a compound of formula II

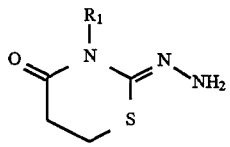

(II)

wherein $R_I$ is as defined above, with an isothiocyanate of formula III

$R_2$—NCS      (III)

or b) reacting a compound of formula X

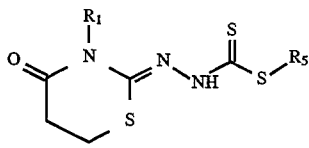

(X)

wherein $R_1$ is as defined above and $R_5$ is a lower alkyl radical, with a corresponding amine of formula IX

$R_2$—NH$_2$      (IX)

wherein $R_2$ is as defined above, and, if desired, separating a mixture of isomers into the individual isomers and isolating the desired isomer and/or converting a resultant salt into the free compound or into another salt.

5. A compound according to claim 1, said compound being selected from the group consisting of 1-(3-Allyl-4-oxo-[1,3]thiazinan-2-ylidene)-4-methylthiosemicarbazone;

1-(3-Allyl-4-oxo-[1,3]thiazinan-2-ylidene)-4-phenylthiosemicarbazone;

1-(3-Allyl-4-oxo-[1,3]thiazinan-2-ylidene)-4-(furan-2-methyl)thiosemicarbazone;

1-(3-Allyl-4-oxo-[1,3]thiazinan-2-ylidene)-4-(thiopene-2-methyl)thiosemicarbazone;

1-(3-Allyl-4-oxo-[1,3]thiazinan-2-ylidene)-4-(tetrahydrofuran-2-methyl)thiosemicarbazone;

1-(3-Allyl-4-oxo-[1,3]thiazinan-2-ylidene)-4-(1-ethoxy-2-acetyl)thiosemicarbazone;

1-(3-Allyl-4-oxo-[1,3]thiazinan-2-ylidene)-4-allylthiosemicarbazone;

1-(3-Allyl-4-oxo-[1,3]thiazinan-2-ylidene)-4-(p-bromophenyl)thiosemicarbazone;

1-(3-Allyl-4-oxo-[1,3]thiazinan-2-ylidene)-4-propynylthiosemicarbazone;

1-(3-Propynyl-4-oxo-[1,3]thiazinan-2-ylidene)-4-methylthiosemicarbazone;

1-(3-Propyl-4-oxo-[1,3]thiazinan-2-ylidene)-4-methylthiosemicarbazone;

1-(3-Methallyl-4-oxo-[1,3]thiazinan-2-ylidene)-4-methylthiosemicarbazone;

1-(3-Allyl-4-oxo-[1,3]thiazinan-2-ylidene)-4-benzoylthiosemicarbazone;

1-(3-Allyl-4-oxo-[1,3]thiazinan-2-ylidene)-4-(2-methylpropionyl)thiosemicarbazone;

1-(3-Allyl-4-oxo-[1,3]thiazinan-2-ylidene)-4-(phenoxycarbonyl)thiosemicarbazone; and 1-(3-Allyl-4-oxo-[1,3]thiazinan-2-ylidene)-4-acetylthiosemicarbazone;

or a pharmaceutically acceptable salt thereof.

6. A method of treating a disease of rheumatoid genesis to an animal in need thereof comprising administration of a pharmacologically effective amount of a compound according to claim 1 to an animal in need thereof.

7. A pharmaceutical composition comprising a compound according to claim 1 and at least one customary pharmaceutical excipient.

* * * * *